(12) United States Patent
Dirauf et al.

(10) Patent No.: US 10,244,997 B2
(45) Date of Patent: Apr. 2, 2019

(54) C-ARM FOR A MEDICAL EXAMINATION DEVICE OR THERAPEUTIC DEVICE

(71) Applicant: Siemens Healthcare GmbH, Erlangen (DE)

(72) Inventors: Franz Dirauf, Ebensfeld (DE); Alexander Kraemer, Irchenrieth (DE); Wolfgang Neuber, Pressath (DE); Patrick Plannerer, Erbendorf (DE); Martin Seifert, Bayreuth (DE); Josef Zeidler, Marktredwitz (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/029,780

(22) Filed: Jul. 9, 2018

(65) Prior Publication Data

US 2019/0008470 A1 Jan. 10, 2019

(30) Foreign Application Priority Data

Jul. 10, 2017 (DE) .................. 10 2017 211 764

(51) Int. Cl.
*A61B 6/00* (2006.01)
*A61N 5/10* (2006.01)

(52) U.S. Cl.
CPC .......... *A61B 6/4441* (2013.01); *A61N 5/1081* (2013.01)

(58) Field of Classification Search
CPC .................... A61B 6/4441; A61N 5/1081
See application file for complete search history.

(56) References Cited

U.S. PATENT DOCUMENTS

| 6,007,243 | A | * | 12/1999 | Ergun | A61B 6/548 378/197 |
| 7,412,029 | B2 | * | 8/2008 | Myles | A61N 5/1049 378/65 |
| 2009/0180592 | A1 | | 7/2009 | Gross et al. | |
| 2012/0219121 | A1 | * | 8/2012 | Simmons | A61B 6/4405 378/198 |
| 2014/0265182 | A1 | * | 9/2014 | Stanton | A61B 6/035 280/30 |

FOREIGN PATENT DOCUMENTS

| DE | 102008003816 U1 | 7/2009 |
| DE | 202015008455 U1 | 1/2016 |

OTHER PUBLICATIONS

German Office Action dated Mar. 19, 2018 for German Application No. 102017211764.8.

* cited by examiner

*Primary Examiner* — Chih-Cheng Kao
(74) *Attorney, Agent, or Firm* — Harness, Dickey & Pierce, P.L.C.

(57) ABSTRACT

A C-arm for a medical examination device or therapeutic device, is designed as a cast metal component. In at least one embodiment, one or more reinforcement profile, extending at least in certain sections along the C-arm, are cast in.

22 Claims, 2 Drawing Sheets

C-ARM FOR A MEDICAL EXAMINATION DEVICE OR THERAPEUTIC DEVICE

PRIORITY STATEMENT

The present application hereby claims priority under 35 U.S.C. § 119 to German patent application number DE 102017211764.8 filed Jul. 10, 2017, the entire contents of which are hereby incorporated herein by reference.

FIELD

At least one embodiment of the invention generally relates to a C-arm for a medical examination device or therapeutic device, which is designed as a cast metal component.

BACKGROUND

Various medical examination devices or therapeutic devices have a C-arm on which corresponding examination or therapeutic equipment, for example a radiation source and a radiation receiver, are arranged, which can be moved in the room via the C-arm. One example of this are X-ray devices having an X-ray radiation source and an X-ray radiation receiver. They are used for acquiring radiographs. The C-arm is conventionally arranged on a moving device, for example a tripod or a multi-axis steering arm, by which, since the tripod or the articulated arm can be moved around several degrees of freedom, it can be moved in the room, so that the equipment arranged on the arm can be positioned in relation to the patient accordingly.

It is known to produce a C-arm of this kind by extrusion and subsequent rolling of the C-arm mold or as a cast metal component, conventionally made of aluminum. The maximum height of the cross-sectional profile of the C-arm is defined inter alia by the isocenter height and the minimum insertion radius. The arm width is in turn defined by the necessary mobility in respect of the angle of movement to be covered.

With different examination or treatment methods, the C-arm is moved around the patient at high speed in order to acquire 3D images in this way. Increasingly higher demands are made in respect of the rigidity and the increase in the natural frequency of the C-arm in order to achieve the desired image quality and in particular quiet running. So the rigidity of the C-arm can be increased, it is necessary to increase the wall thickness accordingly, although this firstly makes production of the C-arm increasingly difficult, and inevitably also leads to a significant increase in weight, in other words, the moved mass increases in this way, and this is disadvantageous. Secondly, the natural frequency would again be reduced, and this is likewise disadvantageous in respect of a stable arm movement.

From DE 10 2008 003 816 A1 an X-ray device comprising a C-arm rotatably mounted on a robotic arm is known, with the interior of the at least partially hollow C-arm being accessible in the interior of the arm from at least one access side to enable integration of at least some of the electronic components used for operation of the radiation source and the radiation receiver. The C-arm, comprising two separate arm sections joined together in order to form the arm shape, has struts arranged in the manner of a framework on the access side.

Furthermore, a hybrid C-arm for a medical imaging device is known from DE 20 2015 008 455 U1, and this has at least one carbon fiber-reinforced plastics material part, which is permanently arranged in or on the wall of the C-arm.

SUMMARY

Embodiments of the invention are therefore based on the problem of disclosing a C-arm that is improved by comparison.

According to at least one embodiment of the invention, a C-arm for a medical examination device or therapeutic device is provided, which is designed as a cast metal component, wherein one or more reinforcement profiles extending along the C-arm at least in certain sections are cast in.

In addition to the C-arm itself, at least one embodiment of the invention also relates to a method for producing such a C-arm in a metal casting method, comprising:

introducing one or more reinforcement profile(s), extending along the finished C-arm at least in certain sections, into a casting mold, and casting the C-arm by embedding the reinforcement profile(s) in the casting mold.

In addition to the method, at least one embodiment of the invention relates to a medical examination device and/or therapeutic device comprising a C-arm of at least one embodiment described.

BRIEF DESCRIPTION OF THE DRAWINGS

Further advantages and details of the present invention result from the example embodiments described below and with reference to the drawings, in which.

DETAILED DESCRIPTION OF THE EXAMPLE EMBODIMENTS

Figure 1:
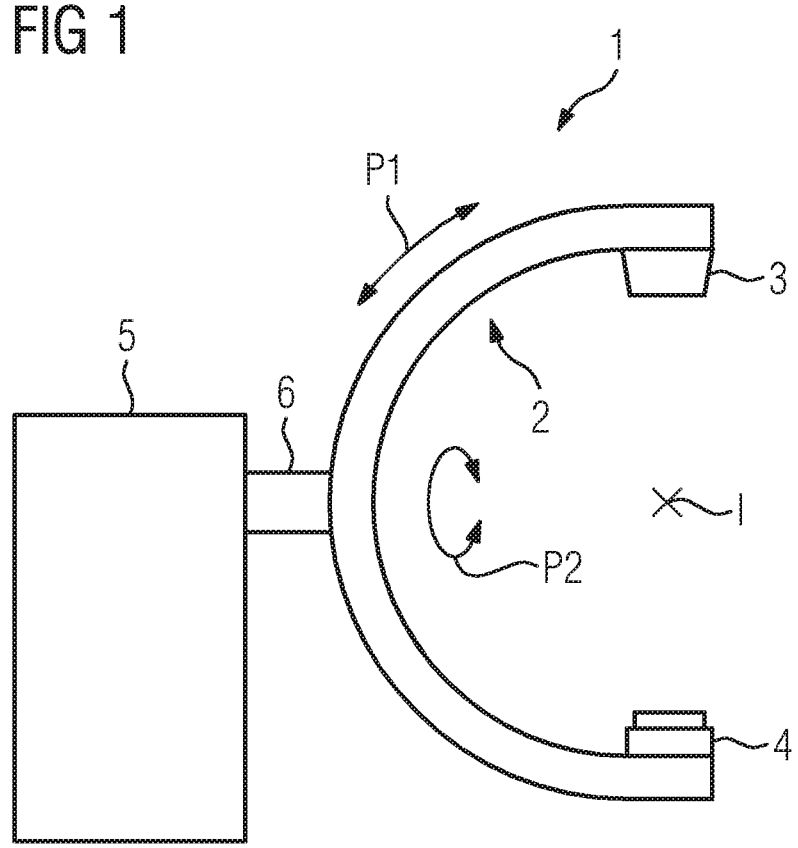
FIG. 1 shows a schematic diagram of an embodiment of an inventive medical examination device or therapeutic device comprising an inventive C-arm.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention, a C-arm for a medical examination device or therapeutic device is provided, which is designed as a cast metal component, wherein one or more reinforcement profiles extending along the C-arm at least in certain sections are cast in.

An inventive C-arm of at least one embodiment, is produced as a cast metal component, preferably made of aluminum. In at least one embodiment, one, preferably a plurality of, reinforcement profile(s) is/are cast into the cast metal component. These reinforcement profiles extend along the C-arm, in other words, are molded according to the arm shape, wherein they preferably extend over almost the entire length of the arm. The rigidity of the C-arm can be significantly increased by the casting in of this/these reinforcement profile(s), which are preferably positioned as far as possible from the neutral fibers of the arm. The increase in weight resulting due to casting in of the reinforcement profiles is acceptable to negligible since the reinforcement profiles make up only a portion of the weight of the arm.

As a consequence of integration or casting in of this or these reinforcement profile(s) the C-arm can be retained in its desired dimension; an increase in the wall thickness or the like in order to increase rigidity is not necessary. Nevertheless, the C-arm is significantly more rigid compared to a purely cast metal component and can readily meet the demands placed on it even for movements at high speeds.

The reinforcement profile(s) is/are preferably hollow profiles, in particular with rectangular or square cross-section, and this advantageously results in only an imperceptible increase in weight.

In order to increase rigidity, the reinforcement profile(s) preferably has/have a modulus of elasticity, which is much higher than that of the cast metal component. This is preferably made of aluminum, while the reinforcement profile(s) are preferably made of steel.

The arm itself preferably has a rectangular hollow cross-section, wherein in this case preferably four reinforcement profiles are provided, which are arranged in a rectangular shape, therefore, in other words, in the region of the corners of the rectangular C-arm. They are consequently located in the region of the boundary fibers and outside of the neutral fibers, and this is advantageous for reinforcement of the arm.

An expedient development provides that two adjacent reinforcement profiles are connected together by one or more connecting element(s). That is to say, cast into the cast metal component is more or less a reinforcing skeleton, in this case comprising a plurality of reinforcement profiles, in particular in the form of the hollow profiles, which are connected together by appropriate connecting elements either just locally or over their entire length. These connecting elements can be connected to the reinforcement profiles by welded or glued joints, they are therefore preferably made of the same material as the reinforcement profiles. Such connecting profiles are for example sheets or panels, which preferably have appropriate through holes to enable the passage of the cast material. Appropriate perforated web sheets or web panels are therefore used, and these connect the reinforcement profiles. In the case of a rectangular cross-sectional shape of the arm, a cast, likewise rectangular reinforcement geometry consequently results.

The inventive C-arm of at least one embodiment is characterized as a whole by significantly increased rigidity when there is bending or torsion stress. The natural frequency can also be increased by the integration of the reinforcement profile(s), optionally also of the reinforcing element(s), and this also has a positive effect on the movement operation and therewith the image acquisition operation. The height of the C-arm profile and therefore the isocenter height can also be reduced while the system rigidity remains constant since, naturally, there is also the possibility of configuring the C-arm so as to be significantly narrower or slimmer due to casting-in of the reinforcing components, with identical, previously given rigidity, and this has an advantageous effect on the arm height and the isocenter height.

In addition to the C-arm itself, at least one embodiment of the invention also relates to a method for producing such a C-arm in a metal casting method, comprising:

introducing one or more reinforcement profile(s), extending along the finished C-arm at least in certain sections, into a casting mold, and casting the C-arm by embedding the reinforcement profile(s) in the casting mold.

Therefore, for the actual arm cast, the reinforcement profile(s), regardless of how they are now specifically formed in cross-section or how far they extend in certain sections around the finished arm, and optionally additional reinforcing elements, which will be discussed below, are introduced into and positioned in the mold. The mold is then filled with the metal, conventionally of course aluminum, so that the corresponding reinforcing components are embedded, and the finished, sufficiently reinforced C-arm is produced.

Preferably hollow profiles, preferably with a rectangular and in particular square cross-section, are used as the reinforcement profile or reinforcement profiles.

The arm itself, as described, is preferably cast from aluminum, while as reinforcement profile or reinforcement profiles those made of steel are used, therefore, in other words, profiles, which have a much higher modulus of elasticity than the cast metal component or the cast material.

The reinforcement profiles are preferably arranged in a rectangular shape and cast in the region of the corners of the C-arm having a rectangular, high cross-section, and this is particularly expedient for increasing rigidity.

Finally, two adjacent reinforcement profiles can be connected together by one or more connecting element(s), which connecting elements are likewise cast in. These connecting elements are preferably also made of the same material as the reinforcement profiles, in other words preferably of steel, and are glued or welded thereto. If for example four reinforcement profiles are positioned in the region of the corners of the arm, then these are connected by appropriate connecting elements, for example to form a rectangular shape, resulting in a more or less rectangular reinforcing skeleton extending preferably along almost the entire length of the arm.

Preferably sheets or panels can be used as connecting profiles, and these are preferably provided with through holes, in other words perforated sheets or perforated panels.

In addition to the method, at least one embodiment of the invention relates to a medical examination device and/or therapeutic device comprising a C-arm of at least one embodiment described.

FIG. 1 shows an embodiment of an inventive medical examination device and/or therapeutic device 1, comprising a C-arm 2, on which in the illustrated example a radiation source 3 and a radiation receiver 4, for example an X-ray source and an X-ray radiation receiver, are arranged. The C-arm 2 is arranged on a base frame 5, to which it is coupled by an appropriate connection 6. This connection 6, which is shown here only in principle, can be for example a multi-articulated arm or a tripod or the like. In any case, the C-arm can be moved in the room by way of this connection 6. It can firstly be moved along its arm path, as shown by the double arrow P1, in other words on an orbital path, so that it can be rotated about the isocenter I. Furthermore, it can also be rotated about an axis, as is shown by the arrow P2.

In the case of an articulated arm, the C-arm 2 can also be moved about further axes, likewise in the case of a tripod. FIG. 1 shows only a purely schematic diagram in order to basically illustrate possible movements of the C-arm. Because these possible movements, in particular the orbital movement, which sometimes occurs very quickly, along the arrow P1, result in corresponding demands on the rigidity of the C-arm 2.

FIG. 1 shows a first example of a C-arm 2 in a cross-sectional view. The C-arm 2 is made from or is designed as a cast metal component 7. It is an aluminum cast part, which is produced in an appropriate casting mold. Corresponding guide projections 8 are shown in the region of the lateral end, and these run on corresponding linear guides 9, which are shown here only by way of example, when the C-arm 2 is moved along the orbital path according to arrow P1.

As can be seen, the C-arm 2 has a hollow rectangular profile, in other words, it is a hollow body. Reinforcement profiles 10 are cast in the region of the four corners of the cast metal component, and these are likewise rectangular hollow profiles and are made of a material which has a much higher modulus of elasticity than cast aluminum material; they are preferably steel profiles. These metal reinforcement profiles 10 are cast or embedded in the cast material in the correspondingly reinforced corner regions of the C-arm 2, in other words, in the region of the edge fibers. They extend at least in certain sections, preferably almost over the entire length, of the C-arm, by which it is stiffened very effectively, so that it also meets high movement demands. The wall thickness of the reinforcement profiles 10 is between 2 and 5 mm.

Figure 3:
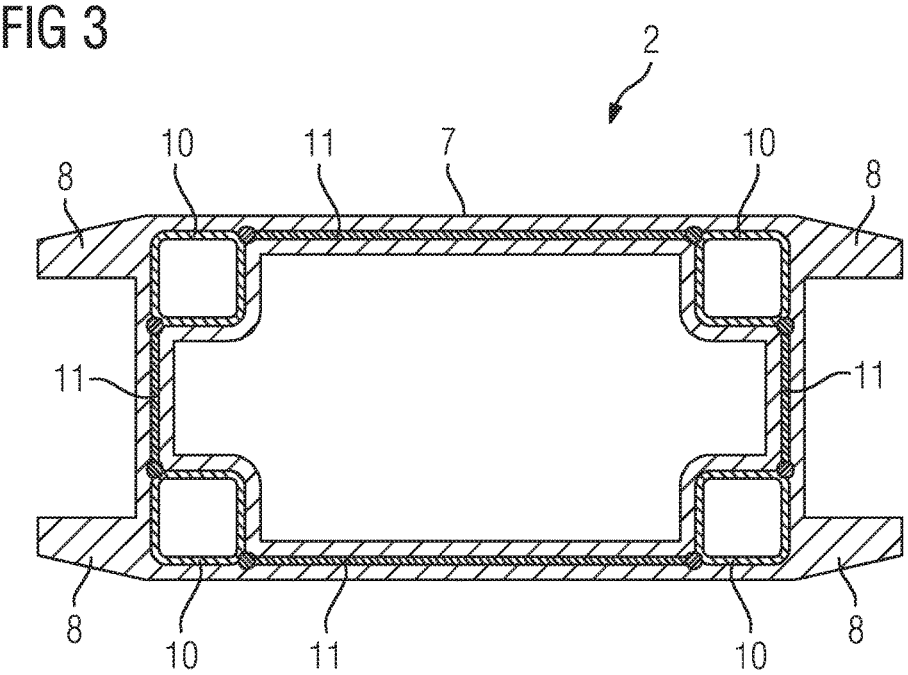
FIG. 3 shows a sectional view through an inventive C-arm of a second embodiment.

FIG. 3 shows a further cross-sectional view through a C-arm 2 of a second inventive embodiment, with identical reference numerals being used for identical components. This C-arm 2 is also designed as a cast metal component 7, in other words, has a cast metal body. Again, appropriate lateral guide portions 8 are provided in the region of the connection 6 for appropriate guidance. The C-arm 2 is also designed here as a hollow body with rectangular cross-sectional shape.

Figure 2:
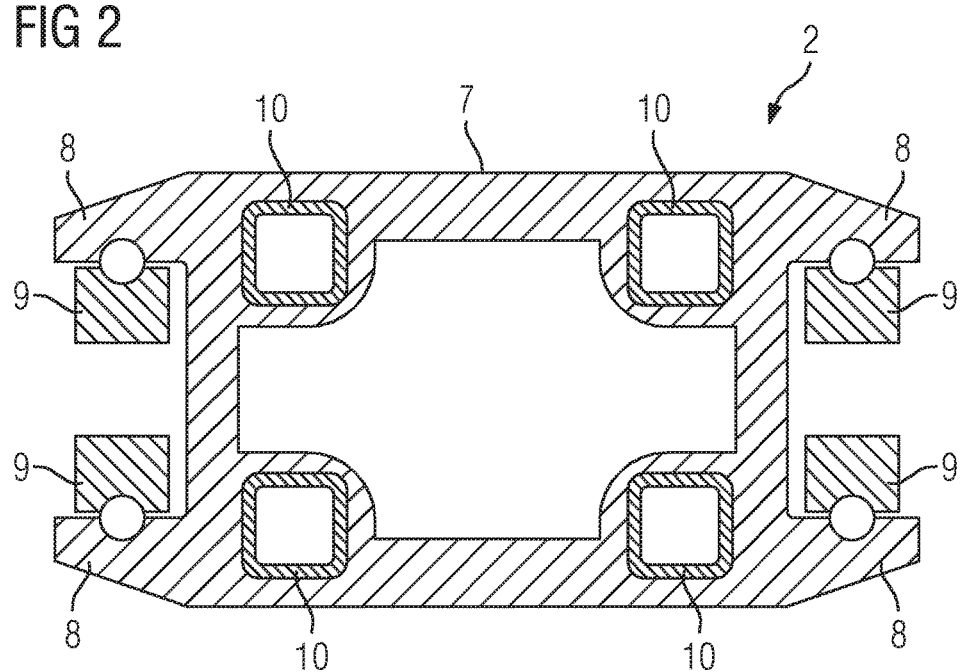
FIG. 2 shows a sectional view through an inventive C-arm of a first embodiment.

As is already the case in the example of FIG. 2, the appropriate rectangular, here likewise square, reinforcement profiles 10 in the form of appropriate hollow bodies are also cast or embedded here in the region of the corners, with the casting compound being provided on all sides here too. Unlike the embodiment of FIG. 1, two adjacent reinforcement profiles 10 are each connected together here, however, by additional reinforcing elements 11 in the form of planar panels or sheets. The connecting elements 11 preferably have a thickness, which matches the thickness of the reinforcement profiles if these are designed as hollow profiles.

The connection is made by welding or gluing, for which purpose the reinforcing elements are preferably made of the same material, therefore likewise of steel, as the hollow reinforcement profiles 10. Viewed along the C-arm, they can connect the reinforcement profiles 10 just locally or in certain sections, but they can also connect them over the entire arm length or profile length. The reinforcing elements 10 are preferably provided with cut-outs, in other words are perforated, so that the cast metal material can penetrate accordingly.

A type of reinforcing skeleton therefore results, which is embedded or cast completely and on all sides in the cast metal body.

For production, the reinforcement profiles 10 and, where present, also the connecting elements already fastened to them, as which appropriately narrow bars can sometimes also be used, are inserted and positioned in an appropriate casting mold, after which the actual casting takes place.

Although the invention has been illustrated and described in detail by the preferred example embodiment, it is not restricted by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A C-arm for a medical examination device or therapeutic device, designed as a cast metal component, the C-arm including one or more reinforcement profiles, extending along the C-arm at least in certain sections, cast in.

2. The C-arm of claim 1, wherein the one or more reinforcement profiles is a hollow profile.

3. The C-arm of claim 2, wherein the cast metal component is made of aluminum and the one or more reinforcement profiles is made of steel.

4. The C-arm of claim 2, wherein the C-arm includes a rectangular hollow cross-section, and wherein the one or more reinforcement profiles includes four reinforcement profiles, arranged in a rectangular shape.

5. The C-arm of claim 4, wherein two adjacent reinforcement profiles are connected together by one or more connecting elements.

6. The C-arm of claim 5, wherein the one or more connecting elements is a sheet or a panel.

7. The C-arm of claim 6, wherein the sheet or panel includes through holes.

8. The C-arm of claim 1, wherein the cast metal component is made of aluminum and the one or more reinforcement profiles is made of steel.

9. The C-arm of claim 1, wherein the C-arm includes a rectangular hollow cross-section, and wherein the one or more reinforcement profiles includes four reinforcement profiles, arranged in a rectangular shape.

10. The C-arm of claim 9, wherein two adjacent reinforcement profiles are connected together by one or more connecting elements.

11. The C-arm of claim 10, wherein the one or more connecting elements is a sheet or a panel.

12. The C-arm of claim 11, wherein the sheet or panel includes through holes.

13. A medical examination device comprising the C-arm of claim 1.

14. A therapeutic device comprising the C-arm of claim 1.

15. A method for producing a C-arm for a medical examination device or therapeutic device, the method comprising:
   introducing one or more reinforcement profiles, extending along the C-arm at least in certain sections, into a casting mold; and
   casting the C-arm by embedding the one or more reinforcement profiles in the casting mold.

16. The method of claim 15, wherein one or more hollow profiles is used as the one or more reinforcement profiles.

17. The method of claim 16, wherein the C-arm is cast from aluminum and wherein the one or more reinforcement profiles is made of steel.

18. The method of claim 15, wherein the C-arm is cast from aluminum and wherein the one or more reinforcement profiles is made of steel.

19. The method of claim 15, wherein the one or more reinforcement profiles are arranged in a rectangular shape and are cast in a region of corners of the C-arm, including a rectangular hollow cross-section.

20. The method of claim 15, wherein the one or more reinforcement profiles include two adjacent reinforcement profiles, connected together by one of more connecting elements, the one or more connecting elements being cast in.

21. The method of claim 20, wherein one or more sheets or one or more panels are used as the one or more connecting elements.

22. The method of claim 21, wherein the one or more sheets or one or more panels include through holes.

\* \* \* \* \*